United States Patent [19]

Pissiotas et al.

[11] 4,425,156

[45] Jan. 10, 1984

[54] PYRIDYL-2-OXYPHENYLOXIME DERIVATIVES, AND THEIR USE AS HERBICIDES

[75] Inventors: Georg Pissiotas, Lörrach, Fed. Rep. of Germany; Hermann Rempfler, Ettingen, Switzerland

[73] Assignee: Ciba-Geigy Corporation, Ardsley, N.Y.

[21] Appl. No.: 340,677

[22] Filed: Jan. 19, 1982

Related U.S. Application Data

[62] Division of Ser. No. 172,575, Jul. 28, 1980, Pat. No. 4,322,241.

[30] Foreign Application Priority Data

Aug. 7, 1979 [CH] Switzerland ................. 7230/79

[51] Int. Cl.$^3$ ............... C07D 213/64; A01N 43/40
[52] U.S. Cl. ................................. 71/94; 546/300; 546/288
[58] Field of Search ................. 546/300; 71/94

[56] References Cited

U.S. PATENT DOCUMENTS 4,133,675  1/1979  Schurter et al. .................. 71/94

Primary Examiner—Alan L. Rotman
Attorney, Agent, or Firm—Frederick H. Rabin

[57] ABSTRACT

The invention relates to novel pyridyl-2-oxy-phenyloxime derivatives of the formula t,0010 wherein Q is an aliphatic or araliphatic ether or ester radical as defined in the specification, $R_1$ is hydrogen, halogen, or a cyano, nitro, lower alkyl or halomethyl group, $R_2$ is halogen, $R_3$ is hydrogen, the nitro or cyano group, n is 0, 1 or 2 and X is hydrogen, halogen or a member selected from the group consisting of cyano, nitro, lower alkyl, lower alkanoyl, carboxylic acid lower alkyl ester or carboxamide. These compounds have good selective herbicidal action, they inhibit plant growth, and they can be employed as safeners for protecting cultivated plants from the phytotoxic action of aggressive agrochemicals.

7 Claims, No Drawings

PYRIDYL-2-OXYPHENYLOXIME DERIVATIVES, AND THEIR USE AS HERBICIDES

This is a divisional of application Ser. No. 172,575 filed on July 28, 1980 now U.S. Pat. No. 4,322,241, Mar. 30, 1982.

The present invention relates to novel pyridyl-2-oxyphenyloxime derivatives, processes for their production, herbicidal and plant growth-regulating compositions of which they are active ingredients, and their use as selective herbicides in crops of cultivated plants.

Pyridyloxy-phenoxyalkanecarboxylic acid derivatives which possess herbicidal and plant growth regulating properties are known from the prior art (e.g. German Offenlegungschrift 2 546 251, 2 649 706 or 2 732 846). Diphenyloximes having herbicidal properties have recently been disclosed in Belgian patent 870 068. The oxime derivatives of the present invention are novel.

The pyridyl-2-oxy-phenyloxime derivatives have the formula I

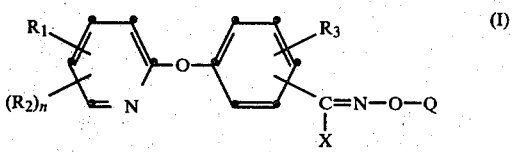

wherein $R_1$ is hydrogen, halogen or a cyano, nitro, lower alkyl or halomethyl group, $R_2$ is halogen, $R_3$ is hydrogen, halogen, the nitro or cyano group, n is 0, 1 or 2, X is hydrogen, halogen or a member selected from the groups consisting of cyano, nitro, lower alkyl, lower alkanoyl, carboxylic acid lower alkyl ester or carboxamide, Q is lower alkyl which is straight-chain or branched or which can be interrupted by heteroatoms or substituted by halogen; lower alkenyl or haloalkenyl; lower alkynyl; $C_3$-$C_7$-cycloalkyl which is unsubstituted or substituted by halogen; lower cyanoalkyl; a lower alkanecarboxylic acid ester group; a lower alkanecarboxylic acid amide group; an aliphatic acyl radical; an araliphatic, cycloaliphatic or unsubstituted or substituted aromatic or heterocyclic acyl radical; an aliphatic, araliphatic, cycloaliphatic or unsubstituted or substituted aromatic or heterocyclic carbonic acid ester radical; an alkylsulfonyl group; a sulfonamide group; a carbamoyl radical.

By halogen in formula I is meant fluorine, chlorine, bromine or iodine.

The term "alkyl" by itself or as moiety of a substituent comprises branched or unbranched $C_1$-$C_8$alkyl groups. Lower alkyl denotes alkyl of 1 to 4 carbon atoms, for example: methyl, ethyl, propyl, isopropyl, butyl, sec-butyl, tert-butyl, and the higher homologues amyl, isoamyl, hexyl, heptyl, octyl together with the isomers thereof. By analogy, cyanoalkyl contains one additional carbon atom and alkanecarboxylic acid ester groups contain at least two additional carbon atoms.

Alkenyl radicals are aliphatic radicals containing one or also two double bonds (alkadienyls) and a maximum of 6, preferably 4, carbon atoms. Haloalkenyl radicals contain not more than 3 halogen atoms, preferably chlorine or bromine atoms. Alkynyl denotes propynyl (=propargyl) and butynyl.

Carboxamide groups comprise also monosubstituted or symmetrically or unsymmetrically disubstituted amides. The substituents can be selected from the group consisting of lower alkyl, lower alkenyl, propynyl or butynyl and also a phenyl ring which can be substituted or unsubstituted.

$C_3$-$C_7$Cycloalkyl groups are cyclopropyl, cyclobutyl, cyclopentyl, cyclohexyl and cycloheptyl. Cycloaliphatic radicals correspond to these ring systems, but, according to circumstances, can contain in addition one or more double bonds.

An araliphatic radical comprises an aryl group, such as unsubstituted or mono-, di- or trisubstituted phenyl, or also naphthyl, fluorenyl, or indanyl, which is bonded to the remainder of the molecule through lower alkyl or lower alkenyl. Examples are benzyl, phenethyl, phenylallyl and homologues.

Aromatic carboxylic acids are derived from aromatics, especially phenyl, and can be substituted. Heterocyclic carboxylic acids are derived from monocyclic or bicyclic rings containing 1 to 3 identical or different heteroatoms O, S and N. Mention may be made of heterocyclic ring systems having 3 to 6, especially 5 or 6, members, which can be saturated, partially saturated or unsaturated, and can be substituted or unsubstituted. Without any limitation being implied, there may be mentioned as examples: furane, nitrofurane, bromofurane, methylfurane, thiophene, chlorothiophene, pyridine, 2,6-dichloropyridine, pyrimidine, pyridazine, pyrazine, piperidine, methylpiperidine, morpholine, thiomorpholine, tetrahydrofurane, oxazole, pyrazole, pyrrole, pyrroline, pyrrolidine, thiazole, 2,3-dihydro-4H-pyrane, pyrane, dioxane, 1,4-oxathi-(2)-ine.

Examples of aliphatic chains interrupted by heteroatoms are: methoxyethyl, ethoxyethyl, propoxyethyl, butoxyethyl, methoxypropyl, ethylthioethyl, methylaminoethyl, tert-butylaminoethyl, alkoxyalkoxyalkyl, such as methoxyethoxyethyl.

A carbamoyl radical (—CO—NH— or —CO—N<) carries at the nitrogen atom one or two radicals selected from the group consisting of lower alkyl, lower alkoxyalkyl, lower alkenyl, lower haloalkenyl, alkynyl or a hydrogen atom, and alternatively a $C_3$-$C_6$cycloalkyl ring or else a phenyl ring which is unsubstituted, or, as in the case of $R_2/R_3$, can be substituted.

Preferred compounds of the formula I are those in which X is the methyl or cyano group and Q is an ester radical

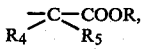

wherein R is lower alkyl, $R_4$ is hydrogen or lower alkyl, $R_5$ is hydrogen, lower alkyl or lower alkoxy, and $R_1$ and $R_2$ are in the 3- and 5-position respectively of the pyridyl ring. In addition, $R_1$ is preferably chlorine or trifluoromethyl, and $R_2$ is chlorine.

When employed in rates of application of 0.5 to 4 kg/ha and more, the pyridyl-2-oxy-phenyloxime derivatives of the formula I have a pronounced herbicidal action against dicotyledonous weeds such as Sida, Sesbania, Amaranthus, Sinapsis, Ipomoea, Galium, Pastinak, Rumex, Matricaria, Chrysanthemum, Abutilon, Solanum etc. However, when employed in higher rates of application of at least 2 to 4 kg/hectare, a number of the compounds act on monocotyledonous weeds, such as Digitaria, Setaria and Echinochloa, whilst monocotyledonous cultivated plants, such as barley, wheat, maize, oats and rice, remain virtually undamaged at lower rates of application and suffer only minor damage at higher rates.

With these compounds it has been possible to obtain good practical results in selectively controlling in particular dicotyledonous weeds in cereals, maize and rice. The active ingredients (compounds of the formula I) and compositions containing them can be employed as contact herbicides in pre-emergence application to sown cultivated areas, but preferably in post-emergence application to weed-infested crops of cultivated plants.

The compositions of the present invention are obtained in known manner by intimately mixing and grinding active ingredients of the general formula I with suitable carriers and/or dispersants, with or without the addition of anti-foam agents, wetting agents, dispersants and/or solvents which are inert to the active ingredients. The active ingredients can be processed to the following formulations:
solid formulations: dust, tracking powders, granules (coated granules, impregnated granules and homogeneous granules),
active ingredient concentrates which are dispersible in water: wettable powders, pastes, emulsions, emulsifiable concentrates:
liquid formulations: solutions.

The compounds of the formula I are obtained by methods which are known per se. In a first method, a 2-halopyridine of the formula II

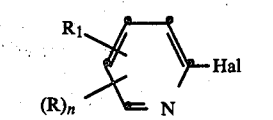
(II)

is reacted with a hydroxybenzaldehyde of the formula III

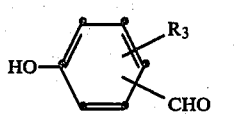
(III)

in the presence of a base, to give a pyridyl-2-oxybenzaldehyde of the formula IV

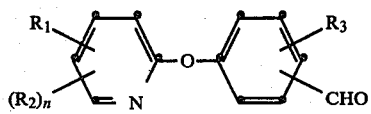
(IV)

which is reduced with sodium borohydride (NaBH$_4$), or a mild reducing agent, to give the pyridyl-2-oxy-benzyl alcohol of the formula V

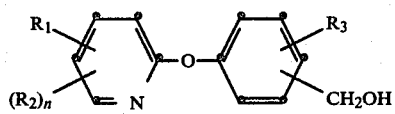
(V)

which is then converted with thionyl chloride, thionyl bromide or phosphoroxy chloride or phosphoroxy bromide to the corresponding pyridyl-2-oxy-benzyl chloride or bromide of the formula VI

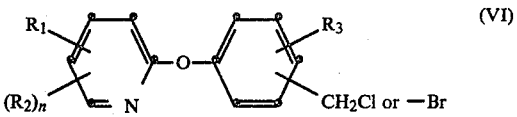
(VI)

This latter compound is then reacted with potassium cyanide or sodium cyanide to give the corresponding cyanomethyl compound of the formula VII

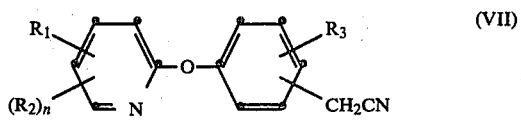
(VII)

which in turn is reacted with isoamyl nitrite (C$_5$H$_{11}$ iso—ON=O), in the presence of sodium methylate (NaOC$_2$H$_5$), to give the pyridyl-2-oxy-phenyl-nitrile oxime salt of the formula VIII

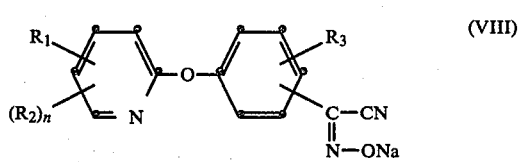
(VIII)

In the above formulae II to VIII, the symbols n, R$_1$, R$_2$ and R$_3$ are as defined for formula I.

One process for the production of the pyridyl-2-oxyphenyloxime derivatives of the formula I, wherein X is cyano, comprises reacting an appropriately substituted pyridyl-2-oxy-phenyl-nitrile oxime salt of the formula VIII above, wherein R$_1$, R$_2$ and R$_3$ have the given meanings, in an inert organic solvent and in the presence of a base, with a compound of the formula IX

Y—Q (IX)

wherein Y is a halogen atom or a removable acid radical and Q has the given meaning.

A further method of obtaining the pyridyl-2-oxyphenyloxime derivatives of the formula I consists in reacting the 2-halopyridine of the formula II with a benzaldehyde or phenyl ketone which is appropriately substituted by R$_3$, in an inert organic solvent and in the presence of a base, to give either the pyridyl-2-oxy-benzaldehyde of the formula IV or a corresponding pyridyl-2-oxy-phenylketone of the formula X

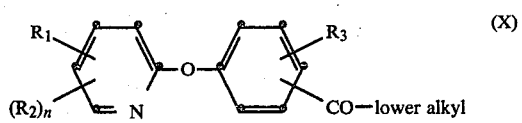
(X)

Reaction of the compound of the formula X with hydroxylamine (H$_2$NOH) yields a pyridyl-2-oxyphenyloxime of the formula XI

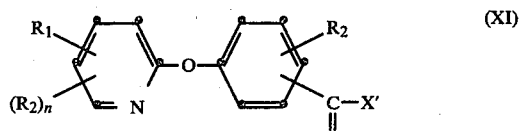
(XI)

wherein X' is hydrogen or lower alkyl. In the formulae X and XI above, n, $R_1$, $R_2$ and $R_3$ are as defined for formula I.

A further process for the production of the pyridyl-2-oxyphenyloxime derivatives of the formula I comprises reacting a pyridyl-2-oxy-phenyloxime of the formula XI above, wherein X' is hydrogen or lower alkyl, and n, $R_1$, $R_2$ and $R_3$ have the given meanings, in an inert organic solvent and in the presence of a base, with a compound of the formula IX, wherein Y is a halogen atom or a removable acid radical and Q has the given meanings, and, if desired, in compounds of the formula I in which X is hydrogen, with appropriate reagents replacing the hydrogen atom by other radicals which fall within the definition of X.

The above reactions are carried out in the temperature range between 0° and 150° C. and in suitable solvents such as acetone, methyl ethyl ketone, acetonitrile, dimethyl formamide, or dimethyl sulfoxide.

Suitable bases are both inorganic bases such as alkali metal hydroxides, carbonates and bicarbonates of alkali metals and alkaline earth metals, and also dry ammonia, as well as organic bases, e.g. tertiary lower alkylamines such as triethylamine, trimethylamine, or also cyclic amines, e.g. pyridine, collidine, or also aromatic amines such as dimethyl aniline.

Examples of removal acid radicals Y are e.g. an alkylsulfonyl group, an arylsulfonyl group, a nitro group, or a halogenated fatty acid radical, e.g. the radical of trichloroacetic acid.

These and other condensation reactions of α-oximino compounds and the alkali metal salts thereof with reactants Y-Q are described in "Organic Reactions", 1953, Vol. 7, pp. 343 and 373.

Oximes always exist in two stereoisomeric forms, the synform and anti-form. Throughout this specification, both stereoisomeric forms shall be understood as existing individually and as mixtures in any ratio.

The following Examples describe the production of a number of compounds (active ingredients) of the formula I. Pressures are in millibars and parts and percentages are by weight.

Example 1

Production of 4-(3',5'-dichloropyridyl-2-oxy)-phenylgloxylonitrile 2-oxime-methylcarbonyl-eth-1''-yl) ether

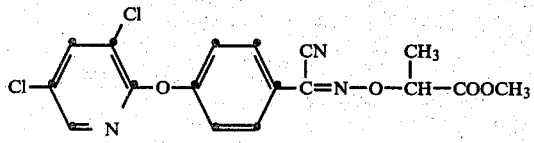

(a) A mixture of 61 g of p-hydroxybenzaldehyde, 81.2 g of 2,3,5-trichloropyridine, 35 g of pulverised potassium hydroxide and 300 ml of dimethyl sulfoxide is stirred in a three-necked flask for 12 hours at 150° C. After cooling, the reaction mixture is poured into an ice-water mixture and extracted with ethyl acetate. The ethyl acetate solution is dried over sodium sulfate and concentrated in vacuo, affording 112 g of 4-(3',5'-dichloropyridyl-2-oxy)-benzaldehyde with a melting point of 78° C.

(b) 13.4 g of 4-(3',5'-dichloropyridyl-2'-oxy)-benzaldehyde are dissolved in 80 ml of methanol and to the solution are added 2 g of sodium borohydride at a temperature between 25° and 30° C. When the reaction is complete, the reaction mixture is stirred for 2 hours at room temperature, then poured into water and extracted with ethyl acetate. The organic phase is dried over sodium sulfate and concentrated, affording 12.1 g of 4-(3',5'-dichloropyridyl-2-oxy)-benzyl alcohol in the form of an oily product with a refractive index of $n_D^{24}$ 1.6133.

(c) 11.3 g of 4-(3',5'-dichloropyridyl-2'-oxy)-benzyl alcohol are dissolved in 50 ml of toluene and to this solution are added dropwise 5 ml of thionyl chloride at room temperature. When the evolution of gas has ceased, the reaction mixture is heated for 2 hours at 100° C. The reaction mixture is concentrated, affording 8 g of 4-(3',5'-pyridyl-2'-oxy)-benzyl chloride in the form of a solid product with a melting point of 73°–75° C.

(d) A mixture of 26 g of 4-(3',5'-dichloropyridyl-2'-oxy)-benzyl chloride, 6.5 g of potassium cyanide and 50 ml of acetonitrile are refluxed for 20 hours. After cooling, the reaction mixture is poured into water. The crystalline precipitate is filtered with suction, washed with water and dried, affording 24.5 g of 4-(3',5'-dichloropyridyl-2'-oxy)-benzyl cyanide with a melting point of 107°–108° C.

(e) With stirring, 6 g of sodium ethylate are dissolved in 80 ml of absolute alcohol in a three-necked flask and the solution is cooled to 0° C. At this temperature, 24.2 g of 4-(2',5'-dichloropyridyl-2'-oxy)-benzyl cyanide are added initially, followed by the dropwise addition of 11.6 ml of isopentyl nitrite at room temperature. The reaction temperature is then stirred for 24 hours at room temperature and the product is precipitated with 200 ml of petroleum ether. The precipitate is collected by filtration, washed with petroleum ether and dried, affording 16.2 g of the sodium salt of 4-(3',5'-dichloropyridyl-2'-oxy)-phenylglyoxylonitrile 2-oxime with a melting point above 280° C.

(f) In a three-necked flask, 12.1 g of the sodium salt of 4-(3',5'-dichloropyridyl-2'-oxy)-phenylglyoxylonitrile-2-oxime are dissolved in 50 ml of dimethyl formamide. Then 4.2 ml of methyl 2-bromopropionate are added dropwise. The reaction mixture is stirred overnight at room temperature, then poured into water and extracted with ether. The ethereal extract is dried and concentrated, affording 12.7 g of the title compound in the form of a brown oil with a refractive index of $n_D^{23}$ 1.5855. (Compound 8).

Example 2

Production of 4-(3',5'-dichloropyridyl-2'-oxy)-acetophenyloxime-(methoxycarbonyl-eth-1''-yl) ether

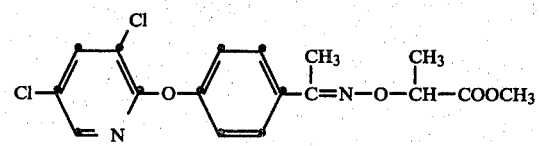

(a) 27 g of 4-(3°,5°-dichloropyridyl-2'-oxy)-acetophenone (obtained by reaction of 2,3,5-trichloropyridine with para-hydroxyacetophenone) are dissolved in 150 ml of alcohol and, after addition of 100 ml of water, 6.6. g of hydroxylamine hydrochloride and 9 g of sodium acetate, the mixture is stirred for 4 hours at a bath temperature of 100° C. After cooling, the precipitated crystalline product is collected by filtration and recrystallised from alcohol, affording 21 g of 4-(3',5'- dichloropyridyl-2'-oxy)-acetophenyloxime with a melting point of 118°–119° C.

(b) 15 g of the oxime obtained in (a) are dissolved in a solution of 70 ml of methanol and 1.2 g of sodium and this solution is evaporated to dryness in vacuo. The salt obtained is dissolved in dimethyl formamide and then 8.5 g of methyl 2-bromopropionate are added dropwise at room temperature. The reaction mixture is stirred for 12 hours, then poured into water and extracted with ethyl acetate. The solution is dried over sodium sulfate and concentrated in vacuo, affording 19 g of the title compound in the form of an oil with a refractive index of $n_D^{23}$ 1.5734 (compound 1).

The following compounds are obtained by methods analogous to those described in the foregoing Examples.

TABLE 1

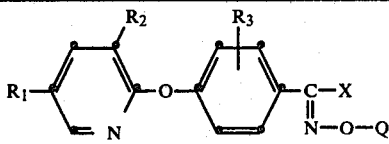

| Compound | $R_1$ | $R_2$ | $R_3$ | X | Q | Physical data (°C.) |
|---|---|---|---|---|---|---|
| 1 | Cl | Cl | H | CH$_3$ | CH(CH$_3$)COOCH$_3$ | $n_D^{23}$ 1.5734 |
| 2 | Cl | Cl | H | CH$_3$ | CONHCH$_3$ | resin |
| 3 | Cl | Cl | H | CH$_3$ | CONHC$_6$H$_5$ | m.p. 113° |
| 4 | Cl | Cl | H | CH$_3$ | CONHC$_6$H$_3$(3,4-Cl) | resin |
| 5 | Cl | Cl | H | CH$_3$ | COC$_6$H$_5$ | m.p. 114° |
| 6 | Cl | Cl | H | CH$_3$ | CH$_2$CN | $n_D^{23}$ 1.5788 |
| 7 | Cl | Cl | H | CH$_3$ | COCH$_3$ | m.p. 115-6° |
| 8 | Cl | Cl | H | CN | CH(CH$_3$)COOCH$_3$ | $n_D^{23}$ 1.5855 |
| 9 | CF$_3$ | Cl | H | CN | CH(CH$_3$)COOCH$_3$ | $n_D^{23}$ 1.5354 |
| 10 | CF$_3$ | Cl | H | CN | CH(CH$_3$)COOC$_2$H$_5$ | |
| 11 | CF$_3$ | Cl | H | CN | CH(CH$_3$)CN | |
| 12 | CF$_3$ | Cl | H | CN | CH(CH$_3$)COOC$_3$H$_7$iso | |
| 13 | CF$_3$ | Cl | H | CN | CH(CH$_3$)COOC$_3$H$_7$n | |
| 14 | CF$_3$ | Cl | H | CN | CH(CH$_3$)COOC$_4$H$_9$iso | $n_D^{23}$ 1.5136 |
| 15 | CF$_3$ | Cl | H | CN | CONHCH$_3$ | |
| 16 | CF$_3$ | Cl | H | CN | CONHC$_6$H$_5$ | |
| 17 | CF$_3$ | Cl | H | CN | COCH$_3$ | |
| 18 | CF$_3$ | Cl | H | CN | COC$_6$H$_4$(4'Cl) | |
| 19 | CF$_3$ | Cl | H | CN | CO(CH$_3$)COOC$_4$H$_9$n | |
| 20 | CF$_3$ | H | H | CN | CH(CH$_3$)COOCH$_3$ | |
| 21 | CClF$_2$ | Cl | H | CN | CH(CH$_3$)COOCH$_3$ | |

TABLE 2

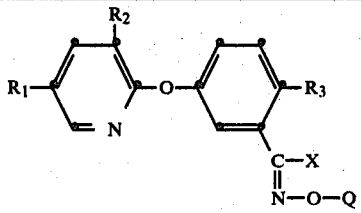

| Compound | $R_1$ | $R_2$ | $R_3$ | X | Q | Physical data |
|---|---|---|---|---|---|---|
| 1 | Cl | Cl | Cl | CN | CH(CH$_3$)COOCH$_3$ | |
| 2 | CF$_3$ | Cl | Cl | CN | CH(CH$_3$)COOCH$_3$ | |
| 3 | Cl | Cl | H | CH$_3$ | CH(CH$_3$)COOCH$_3$ | $n_D^{24}$ 1.5759 |
| 4 | CF$_3$ | Cl | Cl | CH$_3$ | CH(CH$_3$)COOCH$_3$ | |
| 5 | Cl | Cl | Cl | CH$_3$ | COCH$_3$ | |
| 6 | CF$_3$ | Cl | Cl | CH$_3$ | COCH$_3$ | |
| 7 | Cl | Cl | Cl | CH$_3$ | COC$_6$H$_5$ | |
| 8 | CF$_3$ | Cl | Cl | CH$_3$ | COC$_6$H$_5$ | |
| 9 | Cl | Cl | Cl | CH$_3$ | CONHCH$_3$ | |
| 10 | CF$_3$ | Cl | Cl | CH$_3$ | CONHCH$_3$ | |
| 11 | Cl | Cl | Cl | CH$_3$ | CONHC$_6$H$_5$ | |
| 12 | Cl | Cl | Cl | CH$_3$ | CONHC$_6$H$_5$ | |

TABLE 2-continued

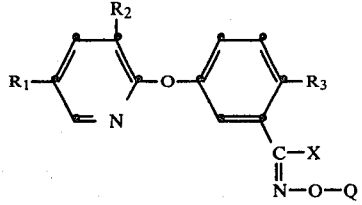

| Compound | $R_1$ | $R_2$ | $R_3$ | X | Q | Physical data |
|---|---|---|---|---|---|---|
| 13 | Cl | Cl | NO$_2$ | CH$_3$ | COOCH$_3$ | |

Example 14

Production of ready-for-use solid and liquid formulations and active ingredient concentrates. Throughout, parts and percentages are by weight.

Granules

The following substances are used to formulate 5% granules:

- 5 parts of 4-(3',5'-dichloropyridyl-2'-oxy)-acetonphenoxime-(methoxycarbonyl)-eth-1"yl) ether.
- 0.25 parts of epoxidised vegetable oil
- 0.25 parts of cetyl polyglycol ether,
- 3.50 parts of polyethylene glycol,
- 91 parts of kaolin (particle size 0.3–0.8 mm).

The active ingredient is mixed with epoxidised vegetable oil dissolved with 6 parts of acetone, and the polyethylene glycol and cetyl polyglycol ether are then added. The resultant solution is sprayed on kaolin and subsequently evaporated in vacuo.

Wettable Powder

The following constituents are used to formulate

| (a) a 70% and (b) a 10% wettable powder: |
| --- |
| (a) 70 parts of 4-(3',5'-dichloropyridyl-2-oxy)-phenylgly-oxalonitrile-2-oxime-methyl-eth-1"-yl) ether,
5 parts of sodium dibutylnaphthylsulfonate,
3 parts of naphthalenesulfonic acid/phenolsulfonic acid/formaldehyde condensate (3:2:1),
10 parts of kaolin,
12 parts of Champagne chalk;
(b) 10 parts of the above active ingredient,
3 parts of a mixture of the sodium salts of saturated fatty alcohol sulfates,
5 parts of naphthalenesulfonic acid/formaldehyde condensate,
83 parts of kaolin. |

The respective active ingredient is applied to the corresponding carriers (kaolin and chalk) and then these are mixed and ground, to yield wettable powders of excellent wettability and suspension powder. By diluting these wettable powders with water it is possible to obtain suspensions containing 0.1 to 80% of active ingredient. These suspensions are suitable for controlling weeds in cultivations of plants.

Paste

The following substances are used to formulate a 45% paste:

| |
| --- |
| 45 parts of 4-(3',5',dichloropyridyl-2'-oxy)-phenylgloxylo-nitirle-2-oxime-methylcarbonyl-eth-1"yl) ether,
5 parts of sodium aluminium silicate,
14 parts of cetyl poylglycol ether with 8 moles of ethylene oxide,
1 part of oleyl polyglycol ether with 5 moles of ethylene oxide,
2 parts of spindle oil,
10 parts of polyethylene glycol,
23 parts of water. |

The active ingredient is intimately mixed with the additives in appropriate devices and ground. By diluting the resultant paste with water, it is possible to prepare suspensions of the desired concentration.

Emulsifiable Concentrate

The following ingredients are mixed to formulate a 25% emulsion concentrate:

| |
| --- |
| 25 parts of 4-(3',5'-dichloropyridyl-2'-oxy)-acetophenyl-oxime-(methoxycarbonyl-eth-1"-yl) ether,
5 parts of a mixture of nonylphenolpolyoxyethylene and calcium dodecylbenzenesulfonate,
15 parts of cyclohexanone,
55 parts of xylene. |

This concentrate can be diluted with water to give emulsions in suitable concentrations of e.g. 0.1 to 10%.

Example 4

The following test methods are employed to establish the usefulness of the compounds of the formula I as pre-emergence and post-emergence herbicides.

Pre-emergence herbicidal action (inhibition of germination)

In a greenhouse, immediately after sowing the test plants in seed dishes, the surface of the soil is treated with an aqueous dispersion of the active ingredients, obtained from a 25% emulsifiable concentrate or from a 25% wettable powder with active ingredients which, on account of their insufficient solubility, cannot be formulated to an emulsifiable concentrate. Four different concentration series were used, corresponding to 4, 2, 1 and 0.5 kg of active ingredient per hectare respectively. The seed dishes are kept in the greenhouse at 22°-25° C. and 50-70% relative humidity, and the test is evaluated 3 weeks later. Compounds 8, 9 and 14 of Table 1 were most effective, especially against dicotyledonous plants in rates of application of 0.5 kg/ha.

Post-emergence herbicidal action (Contact herbicide)

A large number of weeds and cultivated plants, both mono- and dicotyledonous, are sprayed post-emergence in the 4- to 6-leaf stage with an aqueous active ingredient dispersion in rates of 0.125, 0.25 and 0.5 kg of active ingredient per hectare and kept at 24° C.–26° C. and 45–60% relative humidity. The test is evaluated at least 15 days after treatment. Compounds 8, 9 and 14 of Table 1 were most effective, especially against dicotyledonous plants at a rate of application of 0.5 kg/ha.

What is claimed is:

1. A compound of the formula

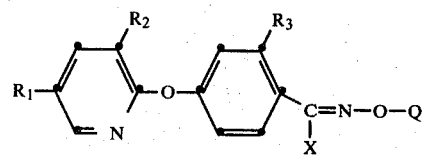

wherein
$R_1$ is halogen or trifluoromethyl,
each of $R_2$ and $R_3$ is hydrogen or halogen,
X is methyl or cyano, and
Q is acetyl, benzoyl or substituted by 1-2 halogen atoms benzoyl.

2. A compound according to claim 1 of the formula

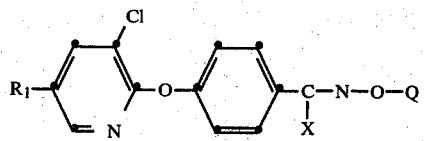

wherein $R_1$ is chlorine or trifluoromethyl.

3. 4-(3,5-Dichloropyridyl-2-oxy)-acetophenyloxime benzoyl ester according to claim 2.

4. 4-(3,5-Dichloropyridyl-2-oxy)-acetophenyloximeacetyl ester according to claim 2.

5. A compound according to claim 1 of the formula

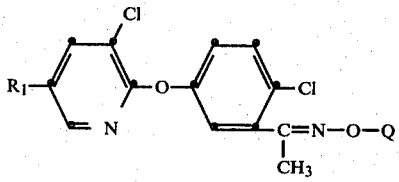

wherein $R_1$ is chlorine or trifluoromethyl, and Q is acetyl or benzoyl.

6. A herbicidal composition which contains (1) as active ingredient a herbicidally effective amount of a compound according to claim 10 and (2) an inert carrier.

7. A method of selectively controlling weeds in crops of cultivated plants, which comprises applying to said crops a herbicidally effective amount of a compound of claims 1, 2 or 5.

* * * * *